United States Patent [19]

Kirino et al.

[11] 4,054,668

[45] Oct. 18, 1977

[54] N-SUBSTITUTED AMINO ACID DERIVATIVES

[75] Inventors: Osamu Kirino, Ashiya; Tadashi Ooishi; Nobuyuki Kameda, both of Takarazuka; Toshiro Kato, Ibaraki; Akira Fujinami, Takarazuka; Toshiaki Ozaki, Toyonaka, all of Japan

[73] Assignee: Sumitomo Chemical Company, Limited, Osaka, Japan

[21] Appl. No.: 619,125

[22] Filed: Oct. 2, 1975

[30] Foreign Application Priority Data

Oct. 2, 1974 Japan .................. 49-114062
Oct. 2, 1974 Japan .................. 49-114063
Oct. 3, 1974 Japan .................. 49-114425
Apr. 4, 1975 Japan .................. 50-41453

[51] Int. Cl.² ............... C07C 101/28; C07C 103/48; A01N 9/24; A01N 9/30
[52] U.S. Cl. .................. 424/314; 424/319; 260/534 R; 560/170; 560/172
[58] Field of Search ............ 260/482 R, 534 R; 424/319, 314

[56] References Cited

U.S. PATENT DOCUMENTS

| 2,700,027 | 1/1955 | Bruson ............... 260/534 R |
| 2,965,534 | 12/1960 | Darlington ............ 424/319 |
| 3,238,236 | 3/1966 | Hauptschein ......... 260/534 R |

FOREIGN PATENT DOCUMENTS

| 37-12261 | 8/1962 | Japan ............... 260/534 R |
| 43-6203 | 3/1968 | Japan ............... 260/534 R |
| 1,048,507 | 11/1966 | United Kingdom ....... 424/319 |

OTHER PUBLICATIONS

Weygand, *Preparative Organic Chemistry*, pp. 448-461 & 468-472, 1972.
Morrison, Organic Chemistry, pp. 722, 743 & 744 (1966).
Speziale, J. Org. Chem., 25, pp. 728-732, (1960).
Supniewski, Chem. Abst., 22:666-3 (1927).

*Primary Examiner*—James O. Thomas, Jr.
*Assistant Examiner*—Michael Shippen
*Attorney, Agent, or Firm*—Sughrue, Rothwell, Mion, Zinn and Macpeak

[57] ABSTRACT

Novel N-substituted amino acid derivatives of the formula:

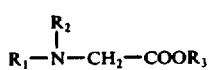

(I)

wherein $R_1$ is an alkenyl group having 2 to 5 carbon atoms, a halogen-substituted alkenyl group having 2 to 5 carbon atoms or an alkynyl group having 2 to 5 carbon atoms, $R_2$ is a methyl or

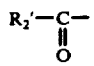

group in which $R_2'$ is an alkyl group having 1 to 4 carbon atoms or a halogen-substituted alkyl group having 1 to 4 carbon atoms; and $R_3$ is a hydrogen atom, an alkyl having 1 to 20 carbon atoms, cycloalkyl having 3 to 6 carbon atoms, benzyl, hydroxyethyl or methoxyethyl group, and inorganic or organic acid addition salts thereof, which possess useful soil fungicidal activities and can be produced by reacting a sarcosine derivative of the formula:

$CH_3HNCH_2COOR_3$  (II)

wherein $R_3$ is as defined above, with a halogen compound of the formula:

$R_1 - X$  (III)

wherein $R_1$ is as defined above and X is a halogen atom, or by reacting an N-substituted glycine derivative of the formula:

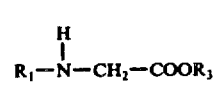

(IV)

wherein $R_1$ and $R_3$ are as defined above, with an acyl compound of the formula:

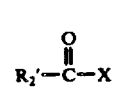

(V)

wherein $R_2'$ is as defined above and X is a halogen atom.

10 Claims, No Drawings

N-SUBSTITUTED AMINO ACID DERIVATIVES

BACKGROUND OF THE INVENTION

1. Field of the Invention

The present invention relates to novel N-substituted amino acid derivatives, and their production and use.

2. Description of the Prior Art

There are known substances which have a chemical structure similar to that of the compounds of this invention. For example, *J. Org. Chem.*, 25, 728 (1960) discloses that N-monosubstituted glycinates have a protective activity against tomato Fusarium wilt.

Further, British Pat. No. 1,048,507 discloses that the N-monosubstituted glycinates have a protective activity against several crop diseases.

However, when such compounds are used in soil treatment procedures against such diseases, the growth of desirable crops is inhibited and marked phytotoxicity appears. Therefore, the prevention of soil-borne plant diseases by the use of such compounds in soil treatments is difficult because marked phytotoxicity to desirable crops is simultaneously caused.

In general, it is difficult to protect agricultural crops against plant pathogens which live in the soil. Soil pathogens live deep in the soil and can withstand environmental changes so that it is not easy to eliminate such microorganisms with pesticides. Further, environmental pollution caused by agricultural chemicals has recently become a serious problem, and therefore, chemicals which are non-toxic to mammals and fish and which do not remain in crops and soil are desired. Several kinds of soil fungicides are now on the market and in use, but some of them are poor in a protective activity and others have high toxicity to mammals. It can safely be said that a completely satisfactory soil fungicide is not yet available on the market.

SUMMARY OF THE INVENTION

For the above reasons, the inventors searched for soil fungicides from various viewpoints and found that the N-substituted amino acid derivatives of the present invention have a high protective activity against a wide range of soil-borne plant diseases without phytotoxicity, and at the same time have the effect of promoting crop growth.

An object of the present invention is to provide N-substituted amino acid derivatives of the formula:

$$R_1-N(R_2)-CH_2-COOR_3 \quad (I)$$

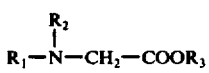

wherein $R_1$ is an alkenyl group having 2 to 5 carbon atoms, a halogen-substituted alkenyl group having 2 to 5 carbon atoms or an alkynyl group having 2 to 5 carbon atoms; $R_2$ is a methyl or

$$R_2'-\underset{\underset{O}{\|}}{C}-$$

group in which $R_2'$ is an alkyl group having 1 to 4 carbon atoms or a halogen-substituted alkyl group having 1 to 4 carbon atoms; and $R_3$ is a hydrogen atom, an alkyl having 1 to 20 carbon atoms, cycloalkyl having 3 to 6 carbon atoms, benzyl, hydroxyethyl or methoxyethyl group and the inorganic or organic acid addition salts thereof.

Preferred compounds of the present invention have the formula:

$$R_1''-N(R_2'')-CH_2-COOR_3'' \quad (I\text{-}a)$$

wherein $R_1''$ is an allyl, chloroallyl, propargyl or crotyl group, $R_2''$ is a methyl or

$$R_2'''-\underset{\underset{O}{\|}}{C}-$$

group in which $R_2'''$ is a methyl, ethyl, n-propyl or monochloro or dichloropropyl group and $R_3''$ is a hydrogen atom, an alkyl having 1 to 18 carbon atoms, cyclohexyl, benzyl, hydroxyethyl or methoxyethyl group and the hydrochlorides, sulfates, acetates or oxalates thereof.

Especially preferred compounds of the present invention have the formula:

$$R_1'-N(R_2')-CH_2-COOR_3' \quad (I\text{-}b)$$

wherein $R_1'$ is an allyl group, $R_2'$ is a methyl group and $R_3'$ is a hydrogen atom, an alkyl having 1 to 3 carbon atoms or a dodecyl group, and the hydrochlorides thereof.

DETAILED DESCRIPTION OF THE INVENTION

When the compounds of the present invention are used in a soil treatment procedure, they are absorbed well by the crops and are widely distributed over the root systems thereof, thus efficiently preventing the attack of pathogens which live deep in the soil. Further, the compounds of this invention gradually decompose in the soil and in plants so that there is no danger of residual chemical build up. The compounds of this invention have little or no toxicity to warm-blooded animals such as mice, rats, chickens and the like, or to fish, so that they cause no harmful environment pollution in this respect. Therefore, it can be said that the present compounds do not cause environmental pollution and are safe for controlling soil-borne plant diseases.

Referring to the fungicidal activity of the present compounds in greater detail, the compounds of this invention have an extremely high controlling effect on plant diseases due to soil pathogens, for example, tomato Fusarium wilt (*Fusarium oxysporum f. lycopersici*), yellows of Japanese radish (*Fusarium oxysporum f. raphani*), cucumber Fusarium wilt (*Fusarium oxysporum f. cucumerinum*), egg plant Verticillium wilt (*Verticillium albo-atrum*), yellows of strawberry (*Fusrium oxysporum*), cotton Fusarium wilt (*Fusarium oxysporum f. vasinfectum*), damping-off of vegetables (*Pythium spp.*), southern blight of vegetables (*Corticium rolfsii*), damping-off of vegetables (*Rhizoctonia solani*), sweet potato violet root rot (*Helicobasidium mompa*), clubroot of vegetables (*Plasmodiophora brassicae*) and the like.

The compounds of the present invention can be used alone without adding other components, or in combination with carriers for ease of use as a pesticide, for example, in conventional forms such as dusts, wettable powders, emulsifiable concentrates, granules, oil sprays, aerosols, fine granules and fumigants. The carriers used can be in the solid, liquid or gas form. Examples of solid carriers include clay, talc, diatomaceous earth, bentonite, kaolin, terra abla and vermiculite; examples of liquid carriers include water, alcohols, ketones, benzene, xylene, toluene, solvent naphtha, petroleum ether and kerosene; and example of gaseous carriers include freon gas, deodorized LPG, methyl chloride, vinyl chloride monomer, dimethyl ether, nitrogen gas and carbon dioxide gas. These preparations can be applied by spraying, dusting or injection in the form of an aqueous dilute solution or without dilution.

Futhermore, the compounds of this invention can be applied in combination with other chemicals, for example, Blasticidin-S, Kasugamycin, Polyoxin, Validamycin, Cellocidin, 3-[2-(3,5-dimethyl-2-oxo-cyclohexyl)-2-hydroxyethyl]glutarimide, Streptomycin, Griseofulvin, pentachloronitrobenzene, pentachlorophenol, hexachlorobenzene, trichloronitromethane, 1,1,1-trichloro-2-nitroethane, dichlorodinitromethane, trichloronitroethylene, 1,1,2,2-tetrachloronitroethane, methylene-bis-thiocyanate, 2,6-dichloro-4-nitroaniline, zinc ethylene-bis-dithiocarbamate, zinc dimethyldithiocarbamate, manganous ethylene-bis-dithiocarbamate, bis-(dimethylthiocarbamoyl)disulfide, 2,4,5,6-tetrachloro-isophthalonitrile, 2,3-dichloro-1,4-naphthoquinone, tetrachloro-p-benzoquinone, p-dimethylaminobenzene diazo sodium sulfonate, 2-(1-methylheptyl)-4,6-dinitrophenyl crotonate, 2-heptadecyl imidazoline acetate, 2,4-dichloro-6-(o-chloroanilino)-S-triazine, dodecylguanidine acetate, 6-methyl-2,3-quinoxaline-dithiol cyclic-S,S-dithiocarbonate, 2,3-quinoxalinedithiol cyclic trithiocarbonate, N-trichloromethylthio-4-cyclohexene-1,2-dicarboxyimide, N-(1,1,2,2-tetrachloroethylthio)-4-cyclohexene-1,2-dicarboxyimide, N-(dichlorofluoromethylthio)-N-(dimethylsulfamoyl)aniline, 1,2-bis-(3-methoxycarbonyl-2-thioureido)benzene, 1,2-bis-(3-ethoxycarbonyl-2-thioureido)-benzene, 2-amino-1,3,4-thiadiazole, 2-amino-5-mercapto-1,3,4-thiadiazole, O-phenylphenol, N-(3,5-dichlorophenyl)maleimide, N-(3,5-dichlorophenyl)succinimide, N-(3,5-dichlorophenyl)-itaconimide, 3-(3',5'-dichlorophenyl)-5,5-dimethyloxazoline-2,4-dione, 2,3-dihydro-5-carboxanilide-6-methyl-1,4-oxathiine-4,4-dioxide, 2,3-dihydro-5-carboxanilide-6-methyl-1,4-oxathiine, 1-(N-n-butylcarbamoyl)-2-methoxycarbonylamino-benzimidazole, O,O-diisopropyl-S-benzyl-phosphorothioate, O-ethyl-S,S-diphenylphosphorodithioate, O-butyl-S-benzyl-S-ethylphosphorodithioate, O-ethyl-O-phenyl-O-(2,4,5-trichlorophenyl)phosphate, O,O-dimethyl-O-(3-methyl-4-nitrophenyl)phosphorothioate, S-[1,2-bis-(ethoxycarbonyl)ethyl]-O,O-dimethylphosphorodithioate, O,O-dimethyl-S-(N-methylcarbamoylmethyl)phosphorodithioate, O,O-diethyl-O-(2-isopropyl-6-methyl-4-pyrimidyl)thiophosphate, 3,4-dimethylphenyl-N-methylcarbamate, iron methane arsonate, ammonium iron methane arsonate, 2-chloro-4,6-bis-(ethylamino)-S-triazine, 2,4-dichlorophenoxy acetic acid (including salts and esters thereof), 2-methyl-4-chlorophenoxy acetic acid (including salts and esters thereof), 2,4-dichlorophenyl-4'-nitrophenyl ether, sodium pentachlorophenolate, N-(3,4-dichlorophenyl)propionamide, 3-(3',4'-dichlorophenyl)-1,1-dimethylurea, α,α,α-trifluoro-2,6-dinitor-N,N-di-n-propyl-p-toluidine, 2-chloro-2',6'-diethyl-N-(methoxymethyl)acetamide, 1-naphthyl-N-methylcarbamate, methyl-N-(3,4-dichlorophenyl)carbamate, 4-chlorobenzyl-N,N-dimethylthiolcarbamate, N,N-diallyl-2-chloroacetamide, O-ethyl-O-(3-methyl-6-nitrophenyl)-N-sec-butylphosphorothioamidate, S-n-butyl-S-(p-tert-butylbenzyl)-N-(3-pyridyl)imidodithiocarbonate and S-n-heptyl-S-(p-tert-butylbenzyl)-N-(3-pyridyl)imidodithiocarbonate.

In the above cases, the individual active ingredient in the mixed preparations does not show a reduction in its own controlling effect, so that it is possible to control two or more kinds of injurious insects at the same time. Further, a synergistic effect due to mixing which is effective for increased practical effects is observed with some combinations. The compounds of this invention can also be used in combination with other agricultural chemicals such as insecticides, fungicides, nematocides, mitocides, herbicides and acaricides, or fertilizers, if desired.

In general, the compounds of this invention can be easily prepared by the following method.

For preparation of N-substituted amino acid derivatives of formula (I) wherein the group $R_2$ is a methyl group, a sarcosine derivative of formula (II):

$$CH_3HNCH_2COOR_3 \qquad (II)$$

wherein $R_3$ is as defined above, is dissolved in a suitable solvent (for example, methyl alcohol, ethyl alcohol, isopropyl alcohol, dioxane, tetrahydrofuran, chloroform, benzene, toluene, xylene, hexane or methyl isobutyl ketone, preferably benzene) and is reacted with a halogen compound of formula (III):

$$R_1 - X \qquad (III)$$

wherein $R_1$ is as defined above and X is a halogen atom, in the presence or absence of a suitable dehydrohalogenating agent (for example, triethylamine, pyridine, dimethylaniline, diethylaniline, N-methylmorpholine, preferably triethylamine). The reaction is carried out, if necessary, under heating or cooling while dropwise adding the halogen compound with stirring. After the reaction is completed, the resulting salt is removed and then the solvent is removed under reduced pressure. Thus, the objective N-substituted amino acid derivative of formula (I) wherein the group $R_2$ is a methyl group can easily be obtained at high yields and at high purity. The purity of the compound can further be increased by operations such as distillation, if desired.

For the preparation of N-substituted amono acid derivatives of formula (I) wherein the group $R_2$ is an $$R_2'-\underset{O}{\overset{\parallel}{C}}-$$

group in which $R_2'$ is as defined above, an N-substituted glycine derivative of formula (IV):

$$R_1-\overset{H}{\underset{|}{N}}-CH_2-COOR_3 \qquad (IV)$$

wherein $R_1$ and $R_3$ are as defined above, is dissolved in a suitable solvent (for example, methyl alcohol, ethyl alcohol, isopropyl alcohol, dioxane, tetrahydrofuran, chloroform, benzene, toluene, xylene, hexane or methyl isobutyl ketone, preferably benzene), and is reacted with an acyl compound of formula (V):

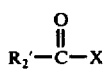
(V)

wherein $R_2'$ is as defined above and X is a halogen atom, in the presence or absence of a suitable dehydrohalogenating agent (for example, triethylamine, pyridine, dimethylaniline, diethylaniline, or N-methylmorpholine, preferably triethylamine). The reaction is carried out, if necessary, under heating or cooling while dropwise adding the acyl compound with stirring. After the reaction is completed, the resulting salt is removed and then the solvent is removed under reduced pressure. Thus, the objective N-substituted amino acid derivative of formula (I) wherein the group $R_2$ is an

group, in which $R_2'$ is as defined above, can easily be obtained at high yields and at high purity. The purity of the compound can further be increased by operations such as distillation, if desired.

When inorganic or organic acid addition salts of the N-substituted amino acid derivative of formula (I) are prepared, the N-substituted amino acid derivative of formula (I) is dissolved in a suitable solvent (for example, water, methyl alcohol, ethyl alcohol, dioxane, tetrahydrofuran, ethyl acetate, chloroform, carbon tetrachloride, benzene, toluene, xylene, hexane, acetone or methyl isobutyl ketone, preferably methyl alcohol), and then there is gradually added to the resulting solution a suitable inorganic or organic acid (for example, hydrochloric acid, sulfuric acid, phosphoric acid, acetic acid, oxalic acid, citric acid, tartaric acid or benzoic acid) with stirring under heating or cooling, if necessary. After the reaction is completed, the solvent is removed under reduced pressure to obtain the objective inorganic or organic acid addition salt of the N-substituted amino acid derivative of formula (I) at high yields and at high purity.

The present invention will now be illustrated by several specific examples and preparation examples in greater detail. However, the present invention is, of course, not to be construed as limited to these examples and preparation examples.

EXAMPLE 1

Into a 100 ml four-necked flask there were placed 11.7 g of sarcosine ethyl ester, 15 g of triethylamine and 50 ml of benzene, and 12.1 g of allyl bromide was gradually added dropwise thereto at room temperature with thorough stirring. The reaction solution was then heated and refluxed for 3 hours. After cooling, the deposited triethylamine hydrobromide was removed by filtration and the benzene removed under reduced pressure. The residue obtained was distilled under reduced pressure to obtain 13.9 g of the objective N-allylsarcosine ethyl ester (b.p.$_{110}$ 116° – 118° C, $n_D^{27.0}$ 1.4308).

| Elementary analysis: | C | H | N |
|---|---|---|---|
| Calculated (%) as $C_8H_{15}NO_2$: | 61.15 | 9.55 | 8.92 |
| Found (%): | 61.01 | 9.37 | 9.08 |

EXAMPLE 2

Into a 100 ml four-necked flask there were placed 17.8 g of N-(3-chloroallyl)glycine ethyl ester, 15.2 g of triethylamine and 50 ml of benzene, and then 16.9 g of γ-chlorobutyryl chloride was gradually dropwise added thereto at room temperature with thorough stirring. Thereafter, the mixture was stirred for 1 hour at 60° C. After cooling, the reaction solution was washed with water, the benzene layer was dried over anhydrous sodium sulfate and the benzene was removed under reduced pressure. The residue obtained was distilled under reduced pressure to obtain 23.7 g of the objective N-(3-chloroallyl)-N-γ-chlorobutyryl glycine ethyl ester (b.p.$_2$ 167 – 170° C, $n_D^{23.0}$ 1.4884).

| Elementary analysis: | C | H | N | Cl |
|---|---|---|---|---|
| Calculated (%) as $C_{11}H_{17}NO_3Cl_2$: | 46.81 | 6.03 | 4.96 | 25.18 |
| Found (%): | 46.66 | 5.95 | 5.19 | 25.32 |

EXAMPLE 3

Into a 100 ml four-necked flask there were placed 14.1 g of N-propargylglycine ethyl ester, 15.2 g of triethylamine and 50 ml of benzene, and then 16.9 g of γ-chlorobutyryl was gradually dropwise added thereto at room temperature with thorough stirring. Thereafter, the mixture was stirred at 60° C for 1 hour. After cooling, the reaction solution was washed with water, the benzene layer was dried over anhydrous sodium sulfate and the benzene was removed under reduced pressure. The residue obtained was distilled under reduced pressure to obtain 19.4 g of the objective N-propargyl-N-γ-chlorobutyryl glycine ethyl ester (b.p.$_2$ 151° – 153° C, $n_D^{25.5}$ 1.4911).

| Elementary analysis: | C | H | N | Cl |
|---|---|---|---|---|
| Calculated (%) as $C_{11}H_{16}NO_3Cl$: | 53.77 | 6.52 | 5.70 | 14.46 |
| Found (%): | 53.53 | 6.49 | 5.83 | 14.80 |

EXAMPLE 4

Two grams of N-allylsarcosine dodecyl ester was dissolved in 20 ml of methyl alcohol and 0.7 g of a 35% aqueous hydrochloric acid solution was gradually dropwise added thereto at room temperature with stirring. After reaction was completed, the methyl alcohol and water were removed under reduced pressure to obtain 2.2 g of the objective N-allylsarcosine dodecyl ester hydrochloride (m.p. 71° – 73° C).

| Elementary analysis: | C | H | N | Cl |
|---|---|---|---|---|
| Calculated (%) as $C_{18}H_{36}NO_2Cl$: | 64.77 | 10.79 | 4.20 | 10.64 |
| Found (%): | 64.63 | 10.98 | 4.05 | 10.91 |

The results obtained by forming other compounds within the scope of the present invention by varying the starting materials while following the above-described method are summarized in Table 1.

TABLE 1

| Compound No. | Chemical Formula | Physical Constant |
|---|---|---|
| (1) | $CH_2=CH-CH_2-\underset{\underset{CH_2-COOH}{|}}{N}-CH_3$ | m.p. 98–101° C |
| (2) | $CH_2=CH-CH_2-\underset{\underset{CH_2-COOC_8H_{17}}{|}}{N}-COCH_3$ | $n_D^{23.5}$ 1.4589 |
| (3) | $CH_2=CH-CH_2-\underset{\underset{CH_2-COOC_{10}H_{21}}{|}}{N}-COCH_2CH_2Cl$ | $n_D^{23.0}$ 1.4867 |
| (4) | $Cl(H)C=CH-CH_2-\underset{\underset{CH_2-COOC_2H_5}{|}}{N}-COCH_2CH_3$ | $n_D^{23.5}$ 1.4713 |
| (5) | $Cl(H)C=CH-CH_2-\underset{\underset{CH_2-COOC_2H_5}{|}}{N}-COCH_2CH_2CH_2Cl$ | $n_D^{23.0}$ 1.4884 |
| (6) | $CH_2=\underset{Cl}{\overset{}{C}}-CH_2-\underset{\underset{CH_2-COOCH_3}{|}}{N}-COCH_2CH_3$ | $n_D^{24.0}$ 1.4830 |
| (7) | $CH_2=CH-CH_2-\underset{\underset{CH_2-COOC_2H_5}{|}}{N}-COCH_2CH_2Cl$ | $n_D^{24.0}$ 1.4774 |
| (8) | $CH_2=CH-CH_2-\underset{\underset{CH_2-COOC_2H_5}{|}}{N}-COCH_2CH_3$ | $n_D^{22.0}$ 1.4762 |
| (9) | $CH\equiv C-CH_2-\underset{\underset{CH_2-COOC_2H_5}{|}}{N}-Cl$ | $n_D^{25.0}$ 1.4901 |
| (10) | $CH_2=CH-CH_2-\underset{\underset{CH_2-COOC_{18}H_{37}}{|}}{N}-\overset{\overset{COCH-CH_2CH_2Cl}{|}}{}\underset{}{Cl}$ | $n_D^{23.5}$ 1.4895 |
| (11) | $CH\equiv C-CH_2-\underset{\underset{CH_2-COOCH_3}{|}}{N}-COCHCH_2CH_3$ | $n_D^{25.5}$ 1.4911 |
| (12) | $CH\equiv C-CH_2-\underset{\underset{CH_2-COOC_2H_5}{|}}{N}-COCH_2CH_2CH_2Cl$ | $n_D^{23.5}$ 1.4331 |
| (13) | $CH_2=CH-CH_2-\underset{\underset{CH_2-COOCH_3}{|}}{N}-CH_3$ | $n_D^{27.0}$ 1.4308 |
| (14) | $CH_2=CH-CH_2-\underset{\underset{CH_2-COOC_2H_5}{|}}{N}-CH_3$ | $n_D^{26.0}$ 1.4392 |
| (15) | $CH_3-CH=CH-CH_2-\underset{\underset{CH_2-COOC_2H_5}{|}}{N}-CH_3$ | $n_D^{26.0}$ 1.4295 |
| (16) | $CH_2=CH-CH_2-\underset{\underset{CH_2-COOCH(CH_3)_{}}{|}}{N}-CH_3$ | $n_D^{24.5}$ 1.4366 |
| (17) | $CH_2=CH-CH_2-\underset{\underset{CH_2-COOC_4H_9}{|}}{N}-CH_3$ | $n_D^{24.5}$ 1.4382 |
| (18) | $CH_2=CH-CH_2-\underset{\underset{CH_2-COOC_5H_{11}}{|}}{N}-CH_3$ | $n_D^{24.5}$ 1.4402 |
| (19) | $CH_2=CH-CH_2-\underset{\underset{CH_2-COOC_6H_{13}}{|}}{N}-CH_3$ | $n_D^{23.5}$ 1.4405 |
| (20) | $CH_2=CH-CH_2-\underset{\underset{CH_2-COOC_7H_{15}}{|}}{N}-CH_3$ | $n_D^{24.5}$ 1.4432 |
| (21) | $CH_2=CH-CH_2-\underset{\underset{CH_2-COOC_8H_{17}}{|}}{N}-CH_3$ | $n_D^{23.5}$ 1.4486 |
| (22) | $CH_2=CH-CH_2-\underset{\underset{CH_2-COOC_{10}H_{21}}{|}}{N}-CH_3$ | $n_D^{25.0}$ 1.4488 |
| (23) | $CH_2=CH-CH_2-\underset{\underset{CH_2-COOC_{11}H_{23}}{|}}{N}-CH_3$ | $n_D^{23.5}$ 1.4492 |
| (24) | $CH_2=CH-CH_2-\underset{\underset{CH_2-COOC_{12}H_{25}}{|}}{N}-CH_3$ | $n_D^{25.0}$ 1.4530 |
| (25) | $CH_2=CH-CH_2-\underset{\underset{CH_2-COOC_{13}H_{27}}{|}}{N}-CH_3$ | $n_D^{25.0}$ 1.4524 |
| (26) | $CH_2=CH-CH_2-\underset{\underset{CH_2-COOC_{14}H_{29}}{|}}{N}-CH_3$ | $n_D^{25.0}$ 1.4529 |
| | $CH_2=CH-CH_2-\underset{\underset{CH_2-COOC_{16}H_{33}}{|}}{N}-CH_3$ | |

TABLE 1-continued

| Compound No. | Chemical Formula | Physical Constant |
|---|---|---|
| (27) | $CH_2=CH-CH_2-\underset{\underset{CH_3}{\mid}}{N}-CH_2-COOC_{18}H_{37}$ | $n_D^{20}$ 1.4542 |
| (28) | $CH_2=CH-CH_2-\underset{\underset{CH_3}{\mid}}{N}-CH_2-COO-C_6H_{11}$ | $n_D^{25}$ 1.4631 |
| (29) | $CH_2=CH-CH_2-\underset{\underset{CH_3}{\mid}}{N}-CH_2-COOCH_2CH_2OH$ | $n_D^{25}$ 1.4630 |
| (30) | $CH_2=CH-CH_2-\underset{\underset{CH_3}{\mid}}{N}-CH_2-COOCH_2CH_2OCH_3$ | $n_D^{20}$ 1.4418 |
| (31) | $CH_2=CH-CH_2-\underset{\underset{CH_3}{\mid}}{N}-CH_2-COOCH_2-C_6H_5$ | $n_D^{25}$ 1.5062 |
| (32) | $CH_3-CH=CH-CH_2-\underset{\underset{CH_3}{\mid}}{N}-CH_2-COOC_{12}H_{25}$ | $n_D^{20}$ 1.4523 |
| (33) | $CH\equiv C-CH_2-\underset{\underset{CH_3}{\mid}}{N}-CH_2-COOC_{10}H_{21}$ | $n_D^{25}$ 1.4495 |
| (34) | $CH\equiv C-CH_2-\underset{\underset{CH_3}{\mid}}{N}-CH_2-COOC_{12}H_{25}$ | $n_D^{25}$ 1.4502 |
| (35) | $Cl(H)C=CH-CH_2-\underset{\underset{CH_3}{\mid}}{N}-CH_2-COOC_{10}H_{21}$ | $n_D^{20}$ 1.4661 |
| (36) | $Cl(H)C=CH-CH_2-\underset{\underset{CH_3}{\mid}}{N}-CH_2-COOC_{12}H_{25}$ | $n_D^{20}$ 1.4669 |
| (37) | $CH_2=\underset{\underset{Cl}{\mid}}{C}-CH_2-\underset{\underset{CH_3}{\mid}}{N}-CH_2-COOC_2H_5$ | $n_D^{20}$ 1.4515 |
| (38) | $CH_2=\underset{\underset{Cl}{\mid}}{C}-CH_2-\underset{\underset{CH_3}{\mid}}{N}-CH_2-COOC_{12}H_{25}$ | $n_D^{25}$ 1.4638 |
| (39) | $CH_2=CH-CH_2-\underset{\underset{CH_3}{\mid}}{N}-CH_2-COOH \cdot HCl$ | m.p. 92–94° C |
| (40) | $CH_2=CH-CH_2-\underset{\underset{CH_3}{\mid}}{N}-CH_2-COOCH_3 \cdot HCl$ | m.p. 73–75° C |
| (41) | $CH_2=CH-CH_2-\underset{\underset{CH_3}{\mid}}{N}-CH_2-COOC_{10}H_{21} \cdot HCl$ | m.p. 53.5–55° C |
| (42) | $(CH_2=CH-CH_2-\underset{\underset{CH_3}{\mid}}{N}-CH_3 \cdot COOC_{10}H_{21})_2 \cdot H_2SO_4$ | $n_D^{25}$ 1.4702 |
| (43) | $CH_2=CH-CH_2-\underset{\underset{CH_3}{\mid}}{N}-CH_2-COOC_{10}H_{21} \cdot CH_3COOH$ | $n_D^{25}$ 1.4446 |
| (44) | $(CH_2=CH-CH_2-\underset{\underset{CH_3}{\mid}}{N}-CH_2-COOC_{10}H_{21})_2 \cdot (COOH)_2$ | m.p. 88–90° C |
| (45) | $CH_2=CH-CH_2-\underset{\underset{CH_3}{\mid}}{N}-CH_2-COOC_{12}H_{25} \cdot HCl$ | m.p. 71–73° C |
| (46) | $(CH_2=CH-CH_2-\underset{\underset{CH_3}{\mid}}{N}-CH_2-COOC_{12}H_{25})_2 \cdot H_2SO_4$ | $n_D^{20}$ 1.4626 |
| (47) | $CH_2=CH-CH_2-\underset{\underset{CH_3}{\mid}}{N}-CH_2-COOC_{12}H_{25} \cdot CH_3COOH$ | $n_D^{20}$ 1.4471 |

EXAMPLE 5

Protective activity on yellows of Japanese radish (*Fusarium oxysporum f. raphani*)

0.1 m² plastic vats were filled with field soil, which was then mixed with soil infested with *Fusarium oxysporum f. raphani* to a depth of 5 cm from the soil surface. Seeds of radish (var.: Wase-40 nichi) were sown on the surface of the soil in each vat (50 per vat) and covered with the soil. An aqueous diluted solution of an emulsifiable concentrate containing a compound of the present invention as shown in Table 2 was then applied to each vat (300 ml per vat). After cultivation in a greenhouse for one month, the disease severity was checked and the percentage of healthy seedlings calculated for each vat according to the following equation.

Percentage of healthy seedlings =

-continued $$\frac{\text{number of healthy seedlings in each treated plot}}{\text{number of germinations in an untreated and uninoculated plot}} \times 100$$

The results obtained are summarized in Table 2. As is apparent from the results, the compounds of this invention have an extremely high protective activity as compared to that of well-known, similar compounds and a commercially available fungicide which were used as controls under the same testing conditions.

TABLE 2

| Test Compound | Concentration of Active Ingredient (ppm) | Percentage of Healthy Seedlings (%) | Phytotoxicity |
|---|---|---|---|
| 1 | 200 | 100.0 | — |
| 2 | " | 94.7 | — |
| 3 | " | 91.3 | — |
| 4 | " | 96.7 | — |
| 5 | " | 100.0 | — |
| 6 | " | 92.7 | — |
| 7 | " | 100.0 | — |
| 8 | " | 88.0 | — |
| 9 | " | 97.3 | — |
| 10 | " | 91.3 | — |
| 11 | " | 100.0 | — |
| 12 | " | 100.0 | — |
| 13 | " | 100.0 | — |
| 14 | " | 96.7 | — |
| 15 | " | 100.0 | — |
| 16 | " | 100.0 | — |
| 17 | " | 100.0 | — |
| 18 | " | 94.7 | — |
| 19 | " | 94.7 | — |
| 20 | " | 91.3 | — |
| 21 | " | 92.7 | — |
| 22 | " | 96.7 | — |
| 23 | " | 100.0 | — |
| 24 | " | 94.7 | — |
| 25 | " | 91.3 | — |
| 26 | " | 92.7 | — |
| 27 | " | 94.7 | — |
| 28 | " | 100.0 | — |
| 29 | " | 96.7 | — |
| 30 | " | 94.7 | — |
| 31 | " | 100.0 | — |
| 32 | " | 100.0 | — |
| 33 | " | 99.3 | — |
| 34 | " | 100.0 | — |
| 35 | " | 91.3 | — |
| 36 | " | 100.0 | — |
| 37 | " | 100.0 | — |
| 38 | " | 100.0 | — |
| 39 | " | 100.0 | — |
| 40 | " | 100.0 | — |
| 41 | " | 99.3 | — |
| 42 | " | 96.7 | — |
| 43 | " | 94.7 | — |
| 44 | " | 97.3 | — |
| 45 | " | 100.0 | — |
| 46 | " | 100.0 | — |
| 47 | " | 100.0 | — |
| (A) $CH_3CH_2CH_2NCH_2COOH$ with $CH_3$ branch | 500 | 22.0 | — |
| (B) phenyl-N(CH₂CN)(C(O)CH₂Cl) | 500 | 21.3 | — |
| (C) benzimidazole-NHCOOCH₃ with CONHC₄H₉-n | 500 | 76.7 | — |
| Inoculated and untreated plot | — | 0.0 | — |
| Uninoculated and untreated plot | — | 100.0 | — |

(A): Bull. Chem. Soc., Japan, 40, 2330 (1969)
(B): Japanese Patent Publication 1433/1971
(C): Commerically available fungicide

EXAMPLE 6

Protective activity on tomato Fusarium wilt (*Fusarium oxysporum f. lycopersici*)

0.1 m² plastic vats were filled with field soil, which was then mixed with soil infested with *Fusarium oxysporum f. lycopersici* to a depth of 5 to 10 cm from the soil surface. Tomato seedlings just under the 2-leaf stage in growth were transplanted in the vats at a rate of 8 per vat. Then, an aqueous diluted solution of an emulsifiable concentrate containing a compound of the present invention as shown in Table 3 was applied to each vat (300 ml per vat). After 10 days, a second application of the compound was carried out in the same manner as the first application. After cultivation in a greenhouse for about one month, the disease severity was checked based on the following standard, and the disease severity was calculated according to the following equation.

| Disease Rating | Degree of Disease |
| --- | --- |
| 0 | Healthy |
| 1 | Less than one-fourth of the stem vessel was brown |
| 2 | One-fourth to one-half of the stem vessel was brown |
| 3 | More than one-half of the stem vessel was brown or dead |

$$\text{Disease severity} = \frac{\Sigma(\text{disease rating} \times \text{number of plants corresponding to the disease rating})}{\text{total number of plants checked} \times 4} \times 100$$

The results obtained are summarized in Table 3. As is apparent from the results, the compounds of this invention have an extremely high protective activity as compared to that of well-known, similar compounds and a commercially available fungicide which were used as controls under the same testing conditions.

TABLE 3

| Test Compound | Concentration of Active Ingredient (ppm) | Disease Severity (%) | Phytotoxicity |
| --- | --- | --- | --- |
| 1 | 200 | 0.0 | — |
| 2 | " | 7.3 | — |
| 3 | " | 3.1 | — |
| 4 | " | 4.2 | — |
| 5 | " | 0.0 | — |
| 6 | " | 2.1 | — |
| 7 | " | 0.0 | — |
| 8 | " | 8.3 | — |
| 9 | " | 7.3 | — |
| 10 | " | 10.4 | — |
| 11 | " | 0.0 | — |
| 12 | " | 0.0 | — |
| 13 | " | 0.0 | — |
| 14 | " | 5.2 | — |
| 15 | " | 0.0 | — |
| 16 | " | 0.0 | — |
| 17 | " | 2.1 | — |
| 18 | " | 4.2 | — |
| 19 | " | 3.1 | — |
| 20 | " | 7.3 | — |
| 21 | " | 4.2 | — |
| 22 | " | 2.1 | — |
| 23 | " | 0.0 | — |
| 24 | " | 8.3 | — |
| 25 | " | 4.2 | — |
| 26 | " | 11.5 | — |
| 27 | " | 12.5 | — |
| 28 | " | 0.0 | — |
| 29 | " | 3.1 | — |
| 30 | " | 4.2 | — |
| 31 | " | 0.0 | — |
| 32 | " | 2.1 | — |
| 33 | " | 3.1 | — |
| 34 | " | 0.0 | — |
| 35 | " | 5.2 | — |
| 36 | " | 0.0 | — |
| 37 | " | 0.0 | — |
| 38 | " | 0.0 | — |
| 39 | " | 0.0 | — |
| 40 | " | 0.0 | — |
| 41 | " | 2.1 | — |
| 42 | " | 5.2 | — |
| 43 | " | 5.2 | — |
| 44 | " | 6.3 | — |
| 45 | " | 0.0 | — |
| 46 | " | 0.0 | — |
| 47 | " | 0.0 | — |
| (A) | | | |
| CH₃CH₂CH₂CH₂N(CH₃)CH₂COOH | 500 | 68.7 | — |
| (B) | 500 | 72.3 | — |
| (C) phenyl-N(CH₂CN)(C(=O)CH₂Cl) | | | |

TABLE 3-continued

| Test Compound | Concentration of Active Ingredient (ppm) | Disease Severity (%) | Phytotoxicity |
|---|---|---|---|
| 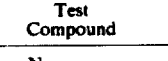 | 500 | 26.0 | — |
| Inoculated and untreated plot | — | 85.5 | — |
| Uninoculated and untreated plot | — | 0.0 | — |

(A): Bull. Chem. Soc., Japan, 40, 2330 (1969)
(B): Japanese Patent Publication 1433/1971
(C): Commercially available fungicide

EXAMPLE 7

Protective activity on club root of vegetables (*Plasmodiophora brassicae*)

0.1 m² plastic vats were filled with field soil, which was then mixed with soil infested with *Plasmodiophora brassicae* to a depth of 10 to 15 cm from the soil surface. Seeds of chinese cabbage (var.: Nozaki No. 2) were sown on the surface of the soil in each vat (about 50 per vat) and covered with the soil. An aqueous diluted solution of an emulsifiable concentrate containing a compound of the present invention as shown in Table 4 was then applied to each vat (300 ml per vat). After ten days, the chinese cabbage seedlings were thinned to a rate of 15 per vat and a second application of the compound carried out in he same manner as the first application. After cultivation in a greenhouse for about one month, the disease level was checked and the percentage of healthy seedlings calculated according to the following equation.

$$\text{Percentage of healthy seedlings} = \frac{\text{number of healthy seedlings in each treated vat}}{\text{total number of test seedlings}} \times 100$$

The results obtained are summarized in Table 4. As is apparent from the results, the compounds of this invention have an extremely high protective activity as compared to that of well-known, similar compounds and a commercially available fungicide which were used as controls under the same testing conditions.

TABLE 4

| Test Compound | Concentration of Active Ingredient (ppm) | Percentage of Healthy Seedlings (%) | Phytotoxicity |
|---|---|---|---|
| 1 | 500 | 100.0 | — |
| 2 | " | 84.5 | — |
| 3 | " | 95.7 | — |
| 4 | " | 82.2 | — |
| 5 | " | 100.0 | — |
| 6 | " | 97.8 | — |
| 7 | " | 100.0 | — |
| 8 | " | 86.7 | — |
| 9 | " | 95.7 | — |
| 10 | " | 93.4 | — |
| 11 | " | 100.0 | — |
| 12 | " | 100.0 | — |
| 13 | " | 100.0 | — |
| 14 | " | 97.8 | — |
| 15 | " | 100.0 | — |
| 16 | " | 100.0 | — |
| 17 | " | 97.8 | — |
| 18 | " | 93.4 | — |
| 19 | " | 93.4 | — |
| 20 | " | 86.7 | — |
| 21 | " | 97.8 | — |
| 22 | " | 97.8 | — |
| 23 | " | 100.0 | — |
| 24 | " | 93.4 | — |
| 25 | " | 84.5 | — |
| 26 | " | 82.2 | — |
| 27 | " | 84.5 | — |
| 28 | " | 97.8 | — |
| 29 | " | 91.1 | — |
| 30 | " | 93.4 | — |
| 31 | " | 100.0 | — |
| 32 | " | 97.8 | — |
| 33 | " | 95.7 | — |
| 34 | " | 100.0 | — |
| 35 | " | 95.7 | — |
| 36 | " | 100.0 | — |
| 37 | " | 100.0 | — |
| 38 | " | 100.0 | — |
| 39 | " | 100.0 | — |
| 40 | " | 100.0 | — |
| 41 | " | 97.8 | — |
| 42 | " | 93.4 | — |
| 43 | " | 93.4 | — |
| 44 | " | 95.7 | — |
| 45 | " | 100.0 | — |
| 46 | " | 100.0 | — |
| 47 | " | 100.0 | — |
| (A) $CH_3CH_2CH_2CH_2\overset{\underset{\mid}{CH_3}}{N}CH_2COOH$ | " | 13.3 | — |
| (B) phenyl-N(CH_2CN)-C(=O)-CH_2Cl | " | 17.8 | — |
| (C) pentachloronitrobenzene | " | 64.5 | — |
| Inoculated and untreated plot | — | 6.7 | — |

(A): Bull. Chem. Soc., Japan, 40, 2330 (1969)
(B): Japanese Patent Publication 1433/1971
(C): Commercially available fungicide

PREPARATION EXAMPLES

1. Dust

Three parts of compound (15) and 97 parts of clay were mixed while powdering to obtain a dust containing 3% of the active ingredient. The product may be applied by dusting, as such, or by mixing with soil.

2. Dust

Four parts of compound (3) and 96 parts of talc were mixed while powdering to obtain a dust containing 4% of the active ingredient. The product may be applied by dusting, as such, or by seed-dressing.

3. Wettable powder

Fifty parts of compound (1), 5 parts of a wetting agent (calcium alkylbenzene sulfonate) and 45 parts of diatomaceous earth were mixed while powdering to obtain a wettable powder containing 50% of the active ingredient. The product may be applied by spraying or dipping in the form of an aqueous dilute solution or by coating without dilution with water.

4. Emulsifiable concentrate

Fifty parts of compound (23), 35 parts of xylene and 15 parts of an emulsifier (polyoxyethylene phenylphenol polymer) were mixed to obtain an emulsifiable concentrate containing 50% of the active ingredient. The product can be applied by spraying in the form of a dilute aqueous solution thereof.

5. Granules

Five parts of compound (39), 93.5 parts of clay and 1.5 parts of Gosenol (a registered trade mark of Nippon Gosei Kagaku Co., Ltd.) were kneaded with water, granulated and dried to obtain granules containing 5% of the active ingredient. The product can be applied by dusting as is.

6. Oil spray 0.5 part of compound (7) and 99.5 parts of kerosene were mixed to obtain an oil spray containing 0.5% of the active ingredient. The product can be applied by spraying as is or by injection.

While the invention has been described in detail and with reference to specific embodiments thereof, it will be apparent to one skilled in the art that various changes and modifications can be made therein without departing from the spirit and scope thereof.

What is claimed is:

1. An N-substituted amino acid derivative of the formula:

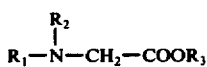

wherein $R_1$ is selected from the group consisting of an allyl, chloroallyl, propargyl or crotyl group; $R_2$ is selected from the group consisting of a methyl or

group in which $R_2'$ is selected from the group consisting of a methyl, ethyl, n-propyl, monochloropropyl or dichloropropyl group and $R_3$ is selected from the group consisting of a hydrogen atom, an alkyl having 1 to 18 carbon atoms, cyclohexyl, benzyl, hydroxyethyl or methoxyethyl group, and the hydrochlorides, sulfates, acetates or oxalates thereof.

2. The N-substituted amino acid derivative according to claim 1, wherein $R_1$ is an allyl group; $R_2$ is a methyl group and $R_3$ is selected from the group consisting of a hydrogen atom, an alkyl having 1 to 3 carbon atoms or a dodecyl group, and the hydrochlorides thereof.

3. The N-substituted amino acid derivative according to claim 1, which is

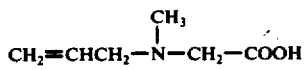

4. The N-substituted amino acid derivative according to claim 1, which is

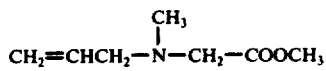

5. The N-substituted amino acid derivative according to claim 1, which is

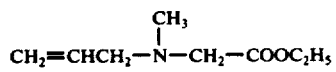

6. The N-substituted amino acid derivative according to claim 1, which is

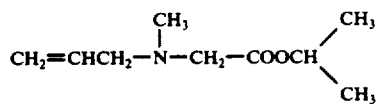

7. The N-substituted amino acid derivative according to claim 1, which is

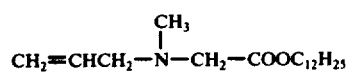

8. The N-substituted amino acid derivative according to claim 1, which is

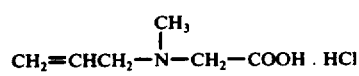

9. The N-substituted amino acid derivative according to claim 1, which is

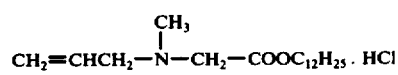

10. A soil fungicidal composition consisting essentially of an inert carrier or diluent and at least one N-substituted amino acid compound of formula (I) as defined in claim 1 as an active ingredient in a fungicidally effective amount.

* * * * *